United States Patent [19]

Sørensen et al.

[11] 4,163,734

[45] Aug. 7, 1979

[54] REFERENCE LIQUID FOR BLOOD GAS EQUIPMENT

[75] Inventors: Søren K. Sørensen, Glostrup; Carl C. Holbek, Allerød, both of Denmark

[73] Assignee: Radiometer A/S, Copenhagen, Denmark

[21] Appl. No.: 866,951

[22] Filed: Jan. 5, 1978

Related U.S. Application Data

[63] Continuation of Ser. No. 652,817, Jan. 27, 1976, abandoned.

[30] Foreign Application Priority Data

May 30, 1975 [DK] Denmark ............................ 2449/75

[51] Int. Cl.$^2$ ................................................ C09K 3/00
[52] U.S. Cl. .................................. 252/408; 23/230 R; 23/230 B; 252/312; 252/316; 424/2; 424/3; 424/350; 424/352
[58] Field of Search ............... 128/2 G, 2 L; 252/408, 252/316, 312; 20/230 B, 230 R, 253 R; 424/2, 3, 352, 350

[56] References Cited

U.S. PATENT DOCUMENTS

| | | | |
|---|---|---|---|
| 3,380,929 | 4/1968 | Petersen | 252/408 |
| 3,466,249 | 9/1969 | Anderson | 252/408 |
| 3,681,255 | 8/1972 | Wilfore | 252/408 |
| 3,778,381 | 12/1973 | Rosano et al. | 252/312 |
| 3,823,091 | 7/1974 | Samejima et al. | 252/312 |
| 3,854,878 | 12/1974 | Kiesow | 23/230 B |
| 3,859,049 | 1/1975 | Ware et al. | 252/408 |
| 3,864,084 | 2/1975 | Folkman | 23/230 B |
| 3,873,267 | 3/1975 | Swartz | 23/230 B |
| 3,874,850 | 4/1975 | Sorensen et al. | 23/230 B |
| 3,884,640 | 5/1975 | Lock et al. | 23/253 R |
| 3,911,138 | 10/1975 | Clark, Jr. | 424/352 |
| 3,964,865 | 6/1976 | Das | 23/230 B |
| 3,993,581 | 11/1976 | Yokoyama et al. | 252/312 |
| 4,116,336 | 9/1978 | Sorensen et al. | 252/408 |

FOREIGN PATENT DOCUMENTS

| | | | |
|---|---|---|---|
| 2236909 | 2/1974 | Fed. Rep. of Germany | 252/408 |
| 1343870 | 1/1974 | United Kingdom | 252/408 |

OTHER PUBLICATIONS

Veefkind, A. H. et al., Clin. Chem., vol. 21, No. 6, pp. 685–693 (1975).
Clark, Jr. et al., Ala. J. Med. Sci., vol. 9, No. 1, pp. 16–29 (1972).
Sargent, J. W. et al., Fed. Proc., vol. 29, No. 5, pp. 1699–1703 (1970).
Osburn, J. O., Fed. Proc., vol. 29, No. 5, pp. 1704–1707 (1970).
Peterson, R. E., Fed. Proc., vol. 29, No. 5, pp. 1714–1716 (1970).

*Primary Examiner*—Benjamin R. Padgett
*Assistant Examiner*—T. S. Gron
*Attorney, Agent, or Firm*—Hubbell, Cohen, Stiefel & Gross

[57] ABSTRACT

A stable synthetic water based reference liquid for quality control and/or calibration of blood gas measuring equipment, said liquid being enclosed in a gas-tight container and containing $HCO_3^-$ ions, $H^+$ ions, $CO_2$ gas, and $O_2$ gas plus an additional pH buffer system different from the pH buffer system constituted by the $HCO_3^-$ ions and the $CO_2$ gas, said liquid showing, at a fixed temperature, known pH, $pCO_2$ and $pO_2$ values, said liquid additionally containing oxygen reversibly contained in a dispersed non-proteinaceous organic substance which shows higher solubility for oxygen than does water, and, optionally, a coloring component showing maximum or significant absorption at about 500 nm, said organic substance being (a) a water-insoluble organic substance in which $O_2$ is soluble to an extent of at least 12% by volume at 1 atmosphere oxygen pressure and 25° C., said water-insoluble substance being a liquid of lipoid character emulsified in a liquid-in-water type emulsion, in the water base of the reference liquid, or a solid suspended in the water base of the reference liquid, or (b) an oxygen complex-forming metal organic compound of a transition group metal dissolved in the water base of the reference liquid, the stability constant of the oxygen complex of which metal organic compound is in the range of $1 \times 10^3$ to $10^{5.5}$.

9 Claims, 3 Drawing Figures

REFERENCE LIQUID FOR BLOOD GAS EQUIPMENT

This is a continuation of application Ser. No. 652,817 filed Jan. 27, 1976 now abandoned.

The present invention relates to a reference liquid for quality control and/or calibration of blood gas measuring equipment.

There are known blood gas measuring apparatuses which are designed for measuring, by means of suitable measuring electrodes, blood pH, concentration of dissolved carbon dioxide in blood, expressed at $P_{O_2}$ (the partial pressure of carbon dioxide) and the concentration of dissolved oxygen in the blood, expressed as $P_{O_2}$ (the partial pressure of oxygen). In addition, and one known fully automatic blood gas measuring apparatus (Radiometer BL1, described, e.g. in U.S. patent application Ser. No. 306,661) also simultaneously measures the blood hemoglobin content (Hb) which is otherwise ordinarily measured separately.

From these four central parameters, there may be calculated various derived parameters which are of great significance in judging the so-called acid-base status of the organism.

The measurements referred to above are all relative measurements where the unknown sample is compared with standards. Hence, the quality of these standards is critical to the quality of the measurement of the individual parameters.

When using manual or semiautomatic blood gas measuring equipment, great technical skill is nowadays a requirement to the user of the measuring equipment in order to obtain measurements of satisfactory quality. The technical level of skill of the user may be lower when a fully automatic self-calibrating equipment is used, e.g., of the type described in the above-mentioned U.S. patent application, but this does not remove the necessity or desirability of being able to check the measuring quality of the equipment, including the quality of the standards, calibration liquids, etc., of the equipment, using a known reference.

Even though it is, in principle, generally known to check a measuring equipment by introducing a sample of known properties into the equipment, this is a great problem in connection with equipment for measuring pH—$P_{CO_2}$, $P_{O_2}$—and optionally Hb.

A sample (a blood sample or another aqueous solution) of this type is normally not stable for long periods ($CO_2$ and $O_2$ escape from the sample) which means that the sample must be prepared on the spot by the user. Normally, this gives rise to problems involving much labor, expensive extra equipment and uncertainty, as the preparation process is technically rather complicated.

All over the world today, there is an interest in a control system for measuring values from equipment of the type mentioned, as this equipment is used directly in connection with patient treatment and often under extremely critical circumstances (e.g. during surgery).

In the U.S.A., Congress has dealt with this problem during recent years, and at present, the legislation tends toward requiring that the "supplier of blood data", e.g. the head doctor of the laboratory, must be able to prove, at any time, that the measuring equipment used is able to yield reliable data in that it has been checked by means of a system independent of the normal calibration system of the equipment (quality control).

Hence, the general desire to-day (also outside the U.S.A.) is that one would be able to buy for this quality control, small containers with samples of known composition and of great reliability.

All blood gas measuring equipment commercially available requires frequent calibration, usually with intervals of some hours. For this purpose, the known art uses, for certain types of equipment, various calibration liquids, some of which (e.g. pH buffer mixtures) are commercially available in small containers and which show high reliability with respect to maintaining the stated pH values, whereas the calibration liquids for the calibration of other parts of the measuring equipment, e.g. the $P_{CO_2}$ measuring equipment and the $P_{O_2}$ measuring equipment, are presently not commercially available in suitable containers and with well-defined data, but well-defined values for pH, $P_{CO_2}$, and $P_{O_2}$, and the above problems. Some technically advanced blood gas measuring equipment, e.g. the above-mentioned fully automatic Radiometer ABL1 blood gas measuring equipment, use solutions which are equilibrated in the equipment per se, with known gas mixtures to obtain well-defined values for pH, $P_{CO_2}$, and $P_{O_2}$, and the calibration liquids thus prepared in the equipment and showing well-defined data are used for the calibration within the equipment, without being transferred to separate containers.

It would be of great interest to be able to perform the very calibration of the blood gas measuring equipment, especially semiautomatic equipment, using a handy reference liquid which may be produced and packed in suitable unit portions and distributed and stored with retention of its relevant data with high exactitude and reliability, in order that the calibration of the blood gas measuring equipment can be performed simply by introducing a unit portion or a part thereof into the equipment without the necessity of any special preparation or checking of the liquid.

Figure 1:
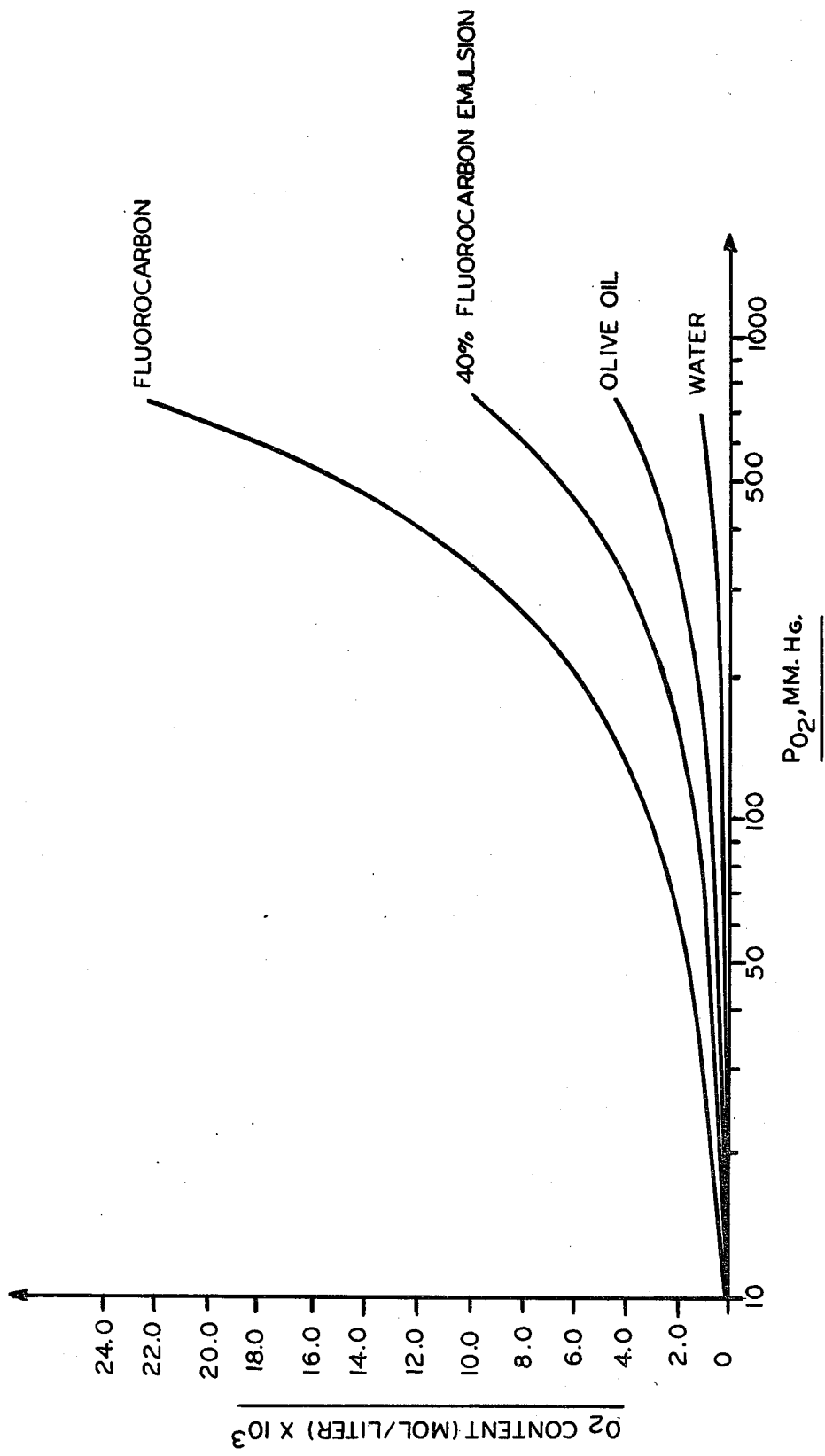
FIG. 1 is a graphical representation showing the molar amount of dissolved oxygen as a function of the partial pressure of oxygen for a number of reference liquids according to the invention.

The present invention provides a reference liquid which may be used for quality control and/or calibration of blood gas measuring equipment, and which is known with respect to the parameters pH, $P_{CO_2}$, $P_{CO_2}$, and, if desired, a parameter representing the hemoglobin concentration.

U.S. Pat. No. 3,681,225 and the specification of Danish patent application No. 1261/72 mention the possibility of using a single calibration liquid with known bicarbonate ion concentration, known partial pressure of carbon dioxide (and consequently in accordance with the known Henderson-Hasselbalch equation, known pH) and known partial pressure of oxygen for calibration of the measuring electrodes in blood gas measuring equipment, and according to the above-mentioned U.S. patent, said calibration liquid may be delivered to the user in a gas-tight container.

Although calibration liquids of this type would, due to the inclusion in a gas-tight container with retention of the known parameters, in principle be suitable for quality control and calibration of blood gas measuring equipment, it is difficult in practice, using the known calibration liquids. In other words in the actual performance of the quality control or calibration by introducing the reference liquid into the blood gas measuring equipment it is difficult to meet such exact requirements which may reasonably be made of a reference liquid for calibration and quality control. Especially, the $P_{O_2}$ control involves serious difficulties, and with the known art calibration liquids contained in gas-tight sealed containers, it is not possible to obtain any reliable control or calibration of the $P_{O_2}$ system under all circumstances.

The reference liquid according to the present invention is contained in a gas-tight container and shows, at a fixed temperature, a known pH; a known partial pressure of carbon dioxide and a known partial pressure of oxygen; and additionally comprises oxygen reversibly contained in a dispersed organic substance which is able to contain, per volume unit, a larger amount of oxygen than water can contain; and optionally a coloring component.

When the reference liquid according to the invention contains a coloring component, it may be used for quality control and/or calibration of the equipment with respect to the determination of the amount of hemoglobin, in addition to the quality control and/or calibration of the equipment with respect to the determination of pH, $P_{CO_2}$ and $P_{O_2}$.

In the reference liquid according to the invention, the problem of unsatisfactory reliability of the control or the calibration of the $P_{O_2}$ system is solved by having the liquid (which is usually an aqueous liquid) comprise oxygen, reversibly contained in a dispersed organic substance which, per volume unit, is able to take up a larger amount of oxygen than is water, in order to increase the $O_2$ capacity. This results in an increased "oxygen buffer capacity", so that any loss or gain of oxygen which may arise during manipulation and measurment, will result in a relatively small change in the $P_{O_2}$ value of the solution, this being the parameter with respect to which the $P_{O_2}$ part of the equipment is to be checked and/or calibrated.

The term "dispersed organic substance" is intended to include both organic substances which are so finely dispersed that a genuine or colloidal solution of the organic substance in the (usually predominantly aqueous) liquid is obtained, and organic substances in emulsion or in suspension in the predominantly aqueous liquid. This meaning may also be expressed by the term "dispersed" covering, in the present context, the three concepts of "dissolved", "emulsified", and "suspended".

The term "reversibly contained" is intended to mean that the oxygen is present in the organic substance in such a manner that the organic substance is able to deliver or take up oxygen under the manipulation and measuring conditions, so that the organic substance will, due to its ability to contain larger amounts of oxygen per volume unit than water, increase the oxygen buffer capacity of the reference liquid. The term "reversibly contained" may include both such cases in which the oxygen is dissolved or otherwise predominantly physically bound in the organic substance, and such cases where the oxygen is predominantly chemically bound, especially complex bound, to or in the organic substance in question. Non-water soluble organic materials showing a great dissolving power for oxygen, are e.g. oils or oily synthetic organic substances and organic polymers. As examples, there may be mentioned silicone oils and silicone rubbers and fluorocarbon compounds, i.e. fluorinated, especially perfluorinated, hydrocarbons and compounds containing such fluorinated hydrocarbon groups, as well as polymers thereof. With such non-water soluble orgaic compounds which are liquids of lipoid character or solid substances, dispersions may be prepared which are emulsions of lipoid-in-water-type or suspensions. For the purpose of the present invention, such systems show the advantage that the great oxygen-dissolving power of the lipoids or solids results in a large oxygen buffer capacity, whereas the liquid still retains its property as an aqueous solution and hence, continuously permits the establishment of a $P_{CO_2}$/pH buffer system. Hence, especially preferred reference liquids according to the invention contain oxygen dissolved in emulsified or suspended non-water soluble organic substances. Of course, it is also possible to use combinations of water soluble and non-water soluble organic substances with large capacities for taking up oxygen.

As an illustration of the increase in solubility for oxygen which is obtained by using one of the substances mentioned, water soluble or non-water soluble, it may be mentioned that the solubility of $O_2$ (at 1 atmosphere's oxygen pressure and 25° C.) in water is 2.4% v/v, while it is, 12% v/v in olive oil, typically 50% v/v in fluorocarbon compounds, typically 18% v/v in silicone rubbers, and typically 20% v/v in silicone oils.

The amount of dissolved oxygen in various systems as function of the partial pressure of oxygen (single logarithmic plot) is shown in FIG. 1 in which "fluorocarbon" designates perfluorotributylamine. It will be noted that while even a very small change in the oxygen amount in pure water will result in a very large difference in $P_{O_2}$, a change of the oxygen amount in, e.g., the fluorocarbon compound will result in a far smaller change in $P_{O_2}$, and that e.g., a 40% emulsion of the fluorocarbon compound in water shows a far better oxygen buffer capacity than water, i.e., shows far less $P_{O_2}$ change per given change in oxygen content.

In this connection it should be noted that almost all substances which increase the ability of the system to dissolve oxygen, will, concomitantly, increase the ability of the system to dissolve carbon dioxide, and, consequently, will increase the carbon dioxide buffer capacity of the system.

When the reference liquid according to the invention is an emulsion or suspension, it is preferred that the emulsified or suspended phase constituted at most 60% of the total volume, especially 20–50%, since the water phase should of course be of a sufficient proportion so as to avoid a decrease in the quality of the pH measurement. Hence, it is clear that in preparing the liquid according to the invention, one will preferably choose such emulsified or suspended components as show an especially high solubility for oxygen, e.g. the above-mentioned fluorocarbon compounds.

As examples of fluorohydrocarbons and fluorohydrocarbon group-containing compounds, in other words fluorocarbon compounds, which are useful for the purpose of the present invention, there may be mentioned perfluorotributyl amine (($C_4F_3$)$_3$N) which is sold by 3M Company under the designation "FC 43", perfluoromethyl cyclohexane and perfluorodimethyl decaline.

Because of its good emulsifying properties and high ability of dissolving oxygen, perfluorotributyl amine is a peferred compound. As an example of a silicone oil useful as emulsified phase in the reference liquid according to the invention there may be mentioned Dow Corning "200 Silicone Oil", and as an example of a silicone rubber useful as suspended phase in the reference liquid according to the invention there may be mentioned silicone rubber CAF4/60 Rhodorsil, Rhône Poulene, Paris.

To obtain a stable emulsion or suspension it may be necessary that the reference liquid according to the invention contain a suitable emulsifying or suspending agent, and this agent may be of any type which does not adversely influence the parameters to be determined by means of the reference liquid, and which also gives a stable emulsion or suspension of the organic material selected. Suitable emulsifiers or suspending agents for this purpose are commercially available. As an example of an emulsifier which has been found to be suitable in the preparation of emulsions of fluorohydrocarbons in water for the purpose of the present invention there may be mentioned Pluriol PE 6800, BASF (polyoxy propylene polyoxy ethylene).

As mentioned above, the organic substance in which the oxygen in the reference liquid according to the invention is reversibly contained may be a substance to which oxygen is reversibly chemically bound, especially complex-bound.

Most chemical processes involving oxygen are characteristic in that the processes are substantially irreversible, so that an oxygen-containing compound once formed will not, to any substantial degree, be able to liberate oxygen or, expressed in another manner, the oxygen-containing compounds formed by the irreversible processes are not suitable for increasing the oxygen buffer capacity of the reference liquids according to the present invention.

However, reversible oxygen processes do exist, e.g. in the blood hemoglobin molecule, which is able to reversibly take up and give off oxygen in substantial amounts and which in principle would therefore be excellently suitable for the purpose of the present invention. However, outside the organism, the hemoglobin molecule is relatively unstable, and reference liquids prepared with hemoglobin as oxygen capacity-increasing organic substance will, therefore, show the disadvantage that they are stable only for relatively short periods unless special precautions are taken to secure their stability, e.g. freezing of the reference liquid immediately or shortly after its preparation and packing, distribution and storing of the reference liquid in frozen form, addition of suitable stabilizers to prevent chemical degradation and suitable sterilization or addition of antibiotics to prevent microbial degradation.

However, other—and simpler and less sensitive—organic compounds than the hemoglobin molecule which are able to reversibly complex-bind oxygen are known. As examples there may especially be mentioned metal organic compounds of transition group metals, especially cobalt or iron, in which the metal is bound, usually complex-bound, to nitrogen-containing groups, e.g. transition group metal complexes with porphyrin-like compounds such as iron(II)phthalocyanine tetrasulfonic acid.

For the purpose of the present invention, the organic substance which is able to chemically bind, especially complex-bind, oxygen reversibly should preferably be one which has a suitable position of the equilibrium of the reversible oxygen reaction in question, i.e. a position of the equilibrium which resembles that of hemoglobin (the greatest resemblance with authentic blood), and/or a position of the equilibrium which results in an optimum oxygen buffer capacity at or about the $P_{O_2}$ value which is to be possessed by the $P_{O_2}$ of the reference liquid.

With respect to the position of the equilibrium of the oxygen reaction of hemoglobin, the following applies when the oxygen uptake of the blood is considered in a simplified manner:

$$Hb + O_2 \rightleftharpoons HbO_2$$

wherein Hb is the hemoglobin molecule, $O_2$ is the oxygen molecule, and $HbO_2$ is the oxygen-containing hemoglobin complex (oxyhemoglobin).

The solubility of oxygen (in free form) in the water phase of blood can reasonably be put at $1.4 \times 10^{-6}$ mole of oxygen per liter per mm Hg oxygen partial pressure. Empirically, at an oxygen partial pressure of 27 mm Hg, equals amounts of hemoglobin in the Hb form, on the one hand, and hemoglobin in $HbO_2$ form on the other hand are present in the blood. At this partial pressure, the concentration of dissolved oxygen in the water phase of blood is:

$$[O_2] = 1.4 \times 10^{-6} \cdot 27 \sim 3.8 \times 10^{-5}.$$

The stability constant K for the oxygen-containing hemoglobin complex is $$K = \frac{[HbO_2]}{[Hb][O_2]}$$

and as (see above) $[HbO_2] = [Hb]$ at $[O_2] \sim 3.8 \times 10^{-5}$, the following applies:

$$K = (1/3.8 \times 10^{-5}) \sim K = 10^{4.5}$$

From this it follows that among the oxygen complex-forming organic compounds binding oxygen in the same manner as hemoglobin, i.e. according to the above reaction scheme, the ideal compounds for use as oxygen buffers in a reference liquid which is very close to the properties of blood in this regard will be such compounds, for which the stability constant of their oxygen complex is about $10^{4.5}$, e.g. in the range of $10^3 - 10^{5.5}$, especially $10^4 - 10^5$.

Another type of (different from hemoglobin) organic compound which reversibly form complexes with oxygen, bind oxygen according to the reaction scheme:

$$2L + O_2 \rightleftharpoons L - O_2 - L$$

wherein L is the ligand which is able to bind oxygen, and $L - O_2 - L$ is the complex compound in its oxygenated form.

The stability constant of the above-mentioned oxygenated complex compound $L - O_2 - L$ is $$K = \frac{[L - O_2 - L]}{[L]^2[O_2]}$$

wherein $[O_2]$ is a concentration of oxygen (in free form) dissolved in the system is question. Like the above calculated stability constant for the oxygenated hemolgobin complex, this constant is, to some extent, temperature dependent; however, for the purpose of the present invention, this temperature dependency can usually be disregarded. When the concentration of L is designated $\alpha$, and the concentration of L—$O_2$—L is designated $\beta$, $\alpha + 2\beta = c$ (cf. the reaction scheme), or $\alpha = c - 2\beta$, $c$ being the total concentration of the ligand. From this follows:

$$\frac{\beta}{\alpha^2 [O_2]} = K = \frac{\beta}{(c - 2\beta)^2 [O_2]}$$
$$\beta = K(c - 2\beta)^2 [O_2] \quad (c - 2\beta)^2 = c^2 + 4\beta^2 - 4c\beta$$
$$\beta = K[O_2]c^2 + 4K[O_2]\beta^2 - 4K[O_2]c\beta$$
$$4K[O_2]\beta^2 - 4K[O_2]c\beta - \beta + K[O_2]c^2 = 0$$
$$4K[O_2]\beta^2 - (4K[O_2]c + 1)\beta + K[O_2]c^2 = 0$$
$$\beta = \frac{(4K[O_2]c + 1)(\pm)\sqrt{(4K[O_2]c + 1)^2 - 16K[O_2]K[O_2]c^2}}{8K[O_2]}$$

wherein $\beta$, as appears from the above, represents the concentration of complex-bound oxygen.

The total oxygen concentration in complex systems, $TO_2$, is $$TO_2 = [O_2] + \beta$$

wherein $[O_2]$ is the concentration of dissolved oxygen, and $\beta$ is the concentration of complex-bound oxygen.

Decisive to the suitability of the oxygen complex-forming compound for use in the liquid according to the invention is that near the oxygen partial pressure which the reference liquid is to possess, a suitable oxygen buffer capacity should be obtained, which means that any loss of small amounts of oxygen from the liquid, or any gain of small amounts of oxygen to the liquid, e.g. during the manipulation of the liquid and during a calibration operation, should result in as small a change in the $P_{O_2}$ of the liquid as possible. A high oxygen buffer capacity is of course in principle obtained when the concentration of the oxygen complex-forming compound in the reference liquid is high, but the oxygen partial pressure around which the buffer effect has its optimum depends on both the concentration mentioned and on the size of the above-mentioned stability constant K. When composing a reference liquid according to the invention using an oxygen complex-forming compound, one should, therefore, preferably select such compound as oxygen complex-forming compound in a concentration such that optimum oxygen buffer capacity is obtained around the oxygen partial pressure to be possessed by the reference liquid. In practice, the oxygen buffer capacity for the above-mentioned complex system can be defined as $$(d\beta/d \log [O_2])$$

wherein $\beta$ and $[O_2]$ are as defined above, and hence, the maximum oxygen buffer capacity is the one at which $$\frac{d^2\beta}{d(\log [O_2])^2} = 0,$$

which for this function is synonymous with $$\frac{d^2 \log [O_2]}{d\beta^2} = 0.$$

As $$\frac{\beta}{(c - 2\beta)^2 [O_2]} = K \text{ it follows that } [O_2] = \frac{\beta}{K(c - 2\beta)^2}$$
$$\log [O_2] = -\log K + \log \beta - 2 \log (c - 2\beta)$$
$$\frac{d \log [O_2]}{d(c - 2\beta)} \cdot \frac{d(c - 2\beta)}{d\beta} = \frac{d \log [O_2]}{d\beta}$$
$$\frac{d \log [O_2]}{d\beta} = \frac{1}{\beta} (\log e) - 2 \frac{1}{c - 2\beta} \log e(-2)$$
$$\frac{d \log [O_2]}{d\beta} = \log e \left( \frac{1}{\beta} + \frac{4}{c - 2\beta} \right)$$
$$\frac{d^2 \log [O_2]}{d\beta^2} = \frac{-\log e}{\beta^2} + \log e(-4(c - 2\beta)^{-2}(-2))$$
$$\frac{d^2 \log [O_2]}{d\beta^2} = \log e \left[ \frac{8}{(c - 2\beta)^2} - \frac{1}{\beta^2} \right]$$

From this follows that $$\frac{d^2 \log [O_2]}{d\beta^2} = 0 \text{ for}$$
$$\frac{8}{(c - 2\beta)^2} = \frac{1}{\beta^2}$$
$$8\beta^2 = (c - 2\beta)^2 = c^2 + 4\beta^2 - 4c\beta$$
$$4\beta^2 + 4c\beta - c^2 = 0$$

$$\beta = \frac{-4c \pm \sqrt{16c^2 + 16c^2}}{8} = \frac{-4c (\pm) 4c\sqrt{2}}{8}$$

$$\beta = \frac{4c(\sqrt{2} - 1)}{8} = \frac{c(\sqrt{2} - 1)}{2} \; 0.207 \cdot c$$

On this basis, there may be calculated, as examples, suitable stability constants for oxygen complexes for use in reference liquids, the oxygen partial pressure of which is to be at one of the three values at which it is often desired to calibrate, i.e. 500 mm Hg, 150 mm Hg, and 50 mm Hg. For these, the following is true:

(1) $[O_2] = 6 \times 10^{-4}$ mol/liter ($\sim$500 mm Hg)
(2) $[O_2] = 2 \times 10^{-4}$ mol/liter ($\sim$150 mm Hg)
(3) $[O_2] = 6 \times 10^{-5}$ mol/liter ($\sim$50 mm Hg)

If it is desired to use the ligand in these cases in a concentration of $c$ $10^{-1}$ mol/liter, the following values are calculated for the stability constant K which at the three $[O_2]$ values mentioned gives maximum oxygen buffer capacity:

$$K = \frac{\beta}{[c - 2\beta]^2 [O_2]} \text{ (cf. above)}$$
$$K = \frac{0.207 \cdot c}{(c - 2 \cdot 0.207 \cdot c)^2 [O_2]} = \frac{0.207 \cdot c}{(0.536 \cdot c)^2 [O_2]}$$
$$K = \frac{0.603}{c \cdot [O_2]}$$
$$K_1 = \frac{0.603}{10^{-1} \times 6 \times 10^4} = 10^4$$
$$K_2 = \frac{0.603}{10^{-1} \times 2 \times 10^{-4}} = 3 \times 10^4$$
$$K_3 = \frac{0.603}{10^{-1} \times 6 \times 10^{-5}} = 10^5$$

Figure 2:
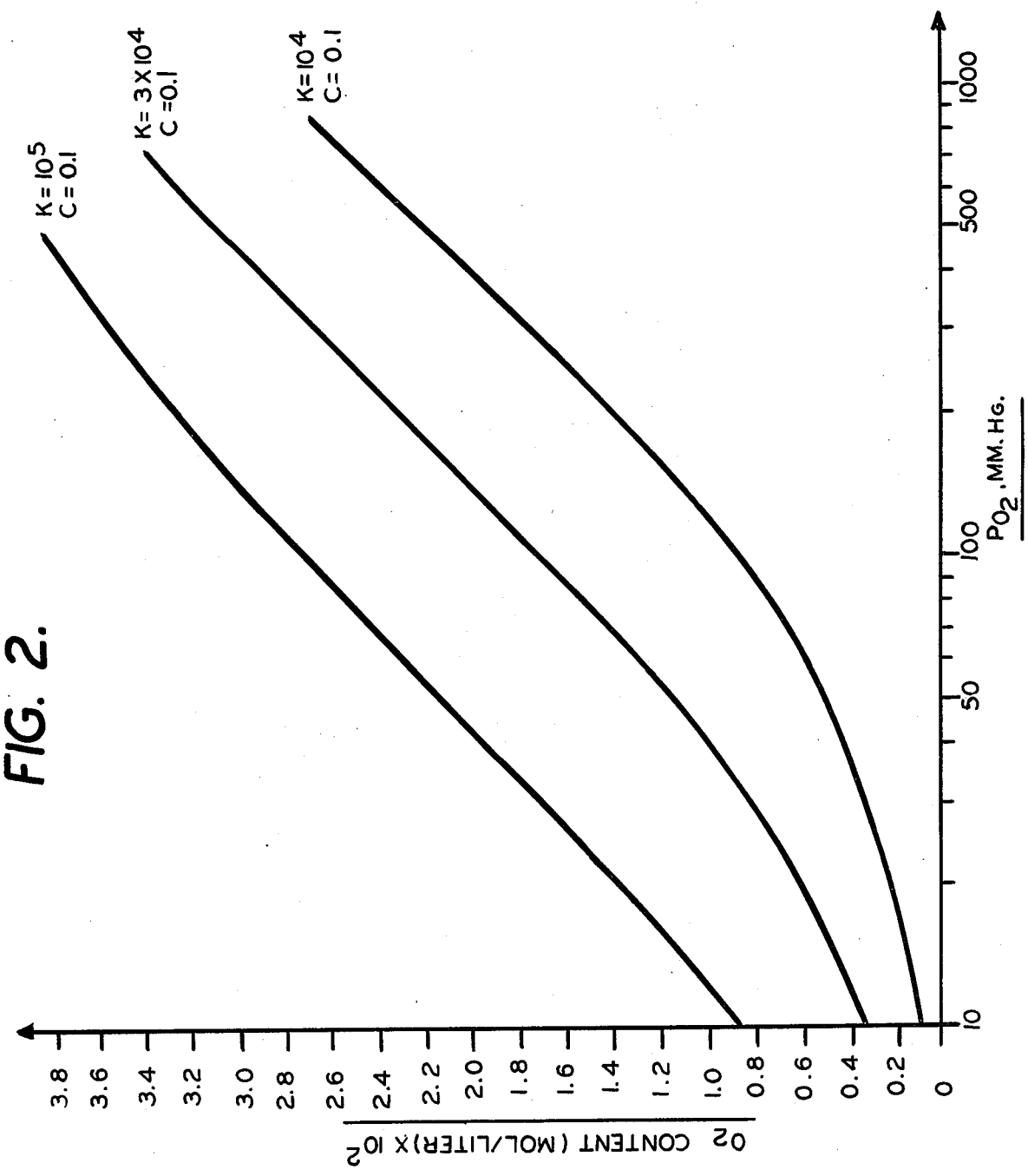
FIG. 2 is a logarithmic plot of the oxygen content of reference liquids according to the invention as a function of the partial pressure of oxygen.

FIG. 2 shows, as a single logarithmic plot, the concentration of total oxygen amount as a function of the partial pressure of oxygen for oxygen complexes with the three above-mentioned stability constants, each of them in a concentration of $10^{-1}$ mol/liter in the reference liquid. It will be seen how the oxygen complex compounds show a considerable oxygen buffer capacity (considerably greater steepness of the graph than for $H_2/$) in a broad range around the partial pressures mentioned, so that loss or gain of a certain amount of oxygen in the range stated will result percent-wise in the same (relatively small) change in the oxygen partial pressure of the system.

On the basis of the examples given above and FIG. 2 it can also be stated that for complex compounds binding oxygen according to the reaction scheme $2L+O_2\rightarrow L-O_2-L$, beneficial stability constants will be in the range of $10^3-10^{5.5}$, especially $10^4-10^5$.

When the reference liquid according to the invention contains, as oxygen buffer capacity-increasing organic substance, an oxygen complex-forming compound, the concentration of this compound is preferably between $10^{-4}$, and 1 mol per liter, especially from $10^{-3}$ to $5\times 10^{-1}$ mol per liter.

Figure 3:
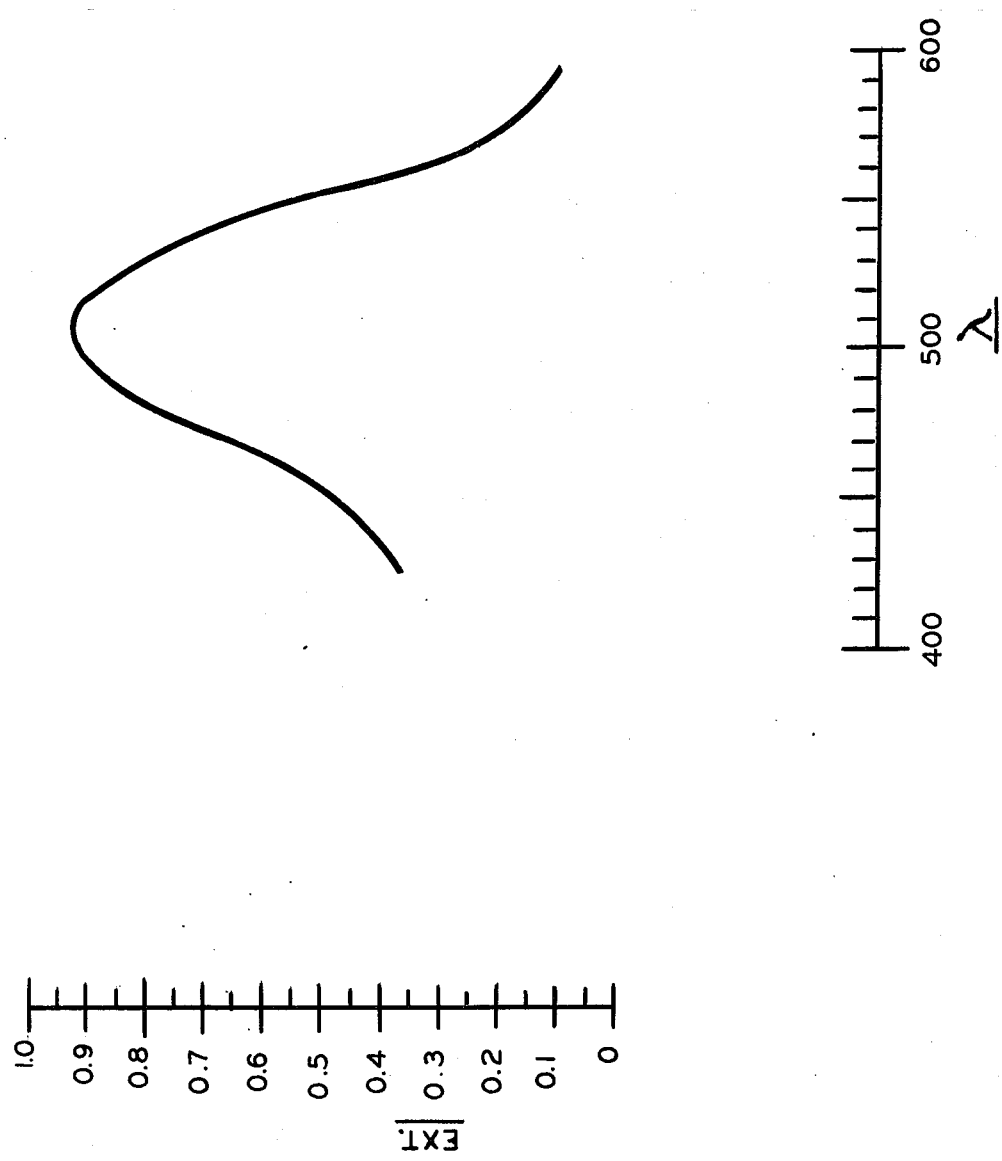
FIG. 3 is a curve showing the absorption of the dyestuff Ponseau 4R.

When the reference liquid according to the invention contains a coloring component which is to "simulate" hemoglobin and permit the use of the reference liquid for quality control and/or calibration of the hemoglobin measuring part of the blood measuring equipment, the coloring component is preferably one having an absorption maximum at or around an isobestic point of the system hemoglobin/hemoglobin-oxygen-complex (in other words, to use the symbols used above, $Hb/HbO_2$), i.e. the point at which the molar extinction caused by Hb has the same size as the molar extinction caused by $HbO_2$, as blood gas measuring equipment comprising a hemoglobin measuring part is usually equipped with such filters that the absorption of the sample introduced is measured at or in a narrow range around one of the isobestic points, e.g. the points at 505 nm. Hence, dyestuffs having an absorption maximum around 500 nm are suitable for use in the reference liquid according to the invention. As examples of such dyestuffs may be mentioned Amaranth, Allura Red and Ponceau 4 R, 70%. The last-mentioned dyestuff is a chemical azo dyestuff having C.I. No. 16,255 (1956). The compound is the trisodium salt of 1-(4-sulfo-1-naphthyl-azo)-2-naphthol-6,8-disulfonic acid. The dyestuff used should suitably be contained in the liquid in such concentration that it corresponds to the extinction of human blood, which, for Ponceau 4 R, 70% means a concentration of about 1.7 g/liter. FIG. 3 shows the absorption curve of Ponceau 4 R.

Until now, the especially characterizing features of the reference liquid according to the invention, viz. the oxygen buffer system and the optional hemoglobin-simulating coloring agent have been explained. In the following, the more conventional properties of the reference liquid, i.e. its pH buffer properties and its $P_{co_2}$ buffer properties will be dealt with.

The establishment of suitable pH and $P_{co_2}$ buffer mixtures pertains to the known art. In principle, one may, in establishing such buffer solutions, utilize the well-known relationship between carbon dioxide dissolved in water and the pH of the solution:

$$pH = pK_A - m\sqrt{\mu} + \log \cdot \frac{[HCO_3^-]}{[CO_2]} \text{ (a modified Henderson-Hasselbalch equation)}$$

wherein $pk_A$ is the thermodynamic dissociation exponent of carbonic acid, m is a constant, $\mu$ is the ionic strength, $[HCO_3^-]$ is the molar concentration of bicarbonate ion, and $[CO_2]$ is the molar concentration of carbon dioxide.

It will thus be seen that the pH of a bicarbonate/carbon dioxide solution is defined and known when the bicarbonate and carbon dioxide concentrations are known. Such systems containing known concentrations of bicarbonate carbonate ion and carbon dioxide may be established in various manners, e.g. by equilibrating a sodium bicarbonate solution with a $CO_2$-containing gas of known partial pressure of $CO_2$, but it is also possible to start from sodium carbonate and form sodium bicarbonate in situ by "titration" with the carbon dioxide, and likewise, it is possible to establish a solution with known bicarbonate ion concentration and known carbon dioxide concentration by adding an acid, such as HCl, to a bicarbonate solution or a carbonate solution. These various procedures and the corresponding calculations of the parameters of the established systems are dealt with in more detail below.

The partial pressure of carbon dioxide in a liquid depends on the concentration of dissolved carbon dioxide in the liquid and of the solubility of carbon dioxide in the liquid in question, in the following manner:

$$[CO_2]_t = k_t P_{co_2}$$

wherein $k_t$ is representative of the solubility of carbon dioxide in the liquid, which solubility is temperature-dependent. A liquid containing a bicarbonate ion-carbon dioxide buffer system (as shown by the above Henderson-Hasselbalch equation) will, hence, show a fixed $P_{co_2}$ at at fixed pH.

For the purpose of the present invention, where it is desirable that the reference liquid retains, to the degree possible, its declared values for pH and $P_{co_2}$ during storing and manipulation, it is desirable to take measures to obtain, to the degree possible, that gain or loss of small amounts of carbon dioxide (during storing and/or manipulation) results in as little change in pH and $P_{co_2}$ as possible, and according to the invention this is achieved by combining the bicarbonate ion-carbon dioxide buffer system with another pH buffer system, according to the invention a phosphate buffer system. Through this, the total buffer effect is increased with respect to the variation of both pH and $P_{co_2}$ at loss or gain of small amounts of carbon dioxide. Hence, preferred reference liquids according to the invention contain both a phosphate buffer system and a bicarbonate ion-carbon dioxide buffer system. In analogy with the above explanation, the establishment of these systems may be obtained in various manners, e.g. by equilibration of a phosphate buffer system with carbon dioxide, by equilibration of a phosphate/carbonate buffer system with $CO_2$, by addition of an acid, for example HCl, to a phosphate/bicarbonate buffer system, or by addition of such an acid to a phosphate/carbonate buffer system. These various methods for establishing such buffer systems also pertain to the known art, but will, however, be discussed in greater detail below.

As most of the parameters with respect to which the reference liquid according to the invention is to be used for quality control and/or calibration, are temperature-dependent, the quality control and/or calibration should be performed at a specific temperature for which the reference liquid is adapted, and the packaging of the reference liquid should state at which temperature or in which temperature range the declared parameter values apply and/or can be guaranteed with a particular uncertainty. In connection with the following explanation of the preparation of the reference liquid it will be understood that one may either prepare and pack the reference liquid at the same temperature as the one at which it is later to be used, or one may prepare and pack the reference liquid at a temperature different from the use temperature and then, by means of physical-chemical calculations and/or empirical corrections, determine the parameter values declared for the use temperature on the basis of the parameter values applying at the preparation temperature.

As mentioned above, the reference liquid according to the present invention must be enclosed in a gas-tight container, and according to the invention it is desirable that the reference liquid be enclosed substantially free of gas phase in the gas-tight container. The reason for this is that a possible difference between the temperature at which the declared data of the reference liquid apply, and the temperature at which the container with the reference liquid is opened or punctured for introduction of the reference liquid into the equipment to be checked or calibrated, will result in less changes in the parameters measured on the reference liquid at the measuring temperature in the cases where the reference liquid is enclosed in its container substantially free of gas phase, than in the cases where there is a substantial gas phase present together with the reference liquid in the gas-tight container.

In practice, the packing of the reference liquid in the gas-tight container will be performed under scrupulously controlled conditions with respect to temperature and pressure, and it is important that the container be totally filled up with liquid. Suitably, the container is to a certain extent flexible so that there will be no separation of a gas phase (micro-bubbles) at varying barometer pressure and temperature during storing, and suitably, the filling of the reference liquid into the container is performed at a reduced pressure, in order to insure that at varying temperature conditions during storing, transportation or in use, e.g. at temperatures between 0° and 50° C., no formation of micro-bubbles due to supersaturation of dissolved gas will take place.

Suitable containers for packing the reference liquid according to the invention are, e.g. ampoules, cannulla-ampoules, tubules (glass cylinders closed at both ends with metallized plastic or rubber stoppers), metal capsules, vials, and preferably tubes with sealed tips or metal foil tubes. The container should be chemically inert to the reference liquid, in order to avoid any changes in the parameters of the reference liquid due to reactions between the components of the reference liquid and the container material. Hence, if the container is of metal, it will be suitable that it be lined with a material which shields the metal from the reference liquid, for example with a plastic foil such as a polyethylene foil.

Hence, a suitable embodiment of the container is for example a continuous metal and plastic foil container which may be the shape corresponding to the known coffee bags, milk cartons (tetrapacks), and shampoo pads, or preferably a plastic-laminated metal tube closed at both ends by welding together the plastic foil. Here, it is essential that the materials and design of the container are so selected that the diffusion through the welding seams is so small that loss of $O_2$ and $CO_2$ during storing, e.g. during as much as two years of storage, will not change the liquid beyond what is acceptable; for most practical utilities, changes of $P_{CO_2}$ and $P_{O_2}$ of at the most about 2%, preferably at the most about 1%, will be acceptable. Furthermore, it is important that the specific material and thickness of the plastic foil are so selected that the amount of $CO_2$ and $O_2$ absorbed in the plastic foil will not influence the measuring results, e.g., assuming that the containers are filled at 37° C. and opened or punctured at about 20° C.

Naturally, the container should be designed in such a manner that the reference liquid may be introduced in a blood gas measuring equipment anaerobically, i.e. without access to atmospheric air, and the known art comprises various suitable designs and adaptors.

The exact process selected in the preparation of the reference liquid will depend on the identity of the systems involved in the reference liquid and, for example, on the method selected for establishing the pH system, see the above explanations. When the oxygen buffer capacity-increasing organic substance is a non-water soluble organic substance showing great solubility for oxygen, and the adjustment of the pH-$P_{CO_2}$ system is performed by equilibration of a buffer system with $CO_2$, a suitable process may for example be one in which the chemicals forming part of the buffer system or systems are weighed out exactly and dissolved in an exactly measured amount of deionized water, the water phase and the organic phase are mixed and emulsified in the desired weight ratio, a very fine emulsion being aimed at, e.g. with an emulsifying level as low as between $10^{-2}\mu$ and $10^{-3}\mu$, if necessary using a suitable emulsifier, the resulting emulsion is transferred to an equilibration tank, suitably a thermostated tank with stirrer and gas jets, the total volume of the tank being suitably 50–100% larger than the volume of the liquid to be equilibrated, said thermostating being performed at suitably 37° C.±0.1° C., and stirring and gas dosing may be performed in a manner so as to ensure a relatively fast equilibration, e.g. an equilibration time of at least 16 hours (overnight), the equilibration is performed with a gas mixture of exactly adjusted and known partial pressure of $CO_2$ and $O_2$, which gas mixture is suitably prepared in a manner known per se using a $CO_2$ gas supply, an $O_2$ gas supply, an $N_2$ gas supply, a pre-moistener and a pressure regulating unit, whereby, e.g. for the equilibration, in the course of 16 hours, of 200 liters of reference liquid which does not per se contain $CO_2$, and with an average utilization of 2% of the gas mixture, there is suitably used a gas flow of about 120 liters/minute, and whereby continuous monitoring of the partial pressure of $CO_2$ and $O_2$ in the gas mixture is performed by means of $P_{CO_2}/P_{O_2}$ electrodes which may be controlled by means of a reference gas measuring equipment, the thus equilibrated reference liquid is filled anaerobically and substantially free of gas phase into the containers, and optionally, sterilization is performed in a manner known per se, e.g. by radioactive irradiation. If addition of acid is used instead of the equilibration with carbon dioxide for establishing $P_{CO_2}$, such as mentioned above, this addition of acid is suitably performed after the equilibration with $O_2$.

The reference liquids prepared and packed in this manner should be carefully checked by taking out samples at suitable intervals and measuring these samples by means of $P_{CO_2}/P_{O_2}$ measuring apparatus, pH equipment, Hb equipment, and total $CO_2/O_2$ measuring equipment, the check on total $CO_2/O_2$ being performed to insure that the $CO_2/O_2$ capacity is in fact present. Officially recognized reference preparations and procedures may be used for the calibration of the measuring equipment in connection with this checking, as is true in connection with the fine adjustment of the production parameters.

When the reference liquid according to the invention is used for quality control, it is, as indicated above, introduced substantially anaerobically into the blood gas measuring equipment, preferably in the same manner and under the same conditions as the blood samples for which the blood gas measuring equipment is designed, the prescriptions given on the packing of the reference liquid being, naturally, carefully adhered to, and the reference liquid passed into the measuring units comprised by the blood gas measuring equipment, usually measuring electrodes and, with respect to the possible hemoglobin unit, usually a photometer. The response of the measuring units on the reference liquid is recorded, and if the recorded values deviate to an unacceptable degree from the declared values of the reference liquid, the problems must be analysed in order to ascertain and remedy errors in the blood gas measuring equipment and/or its calibration liquids and/or the procedure for operating the blood gas measuring equipment.

When the reference liquid according to the invention is used for calibrating blood gas measuring equipment, it is introduced anaerobically into the measuring units of the blood gas measuring equipment, whereby the prescriptions given on the packing of the reference liquid are naturally carefully adhered to, and the measuring equipment is adjusted until there is conformity between the values read from the blood gas measuring equipment and the values declared on the reference liquid. In using the principle of the present invention for calibration, the most suitable way will be to calibrate the blood gas measuring equipment with two different reference liquids according to the invention with values differing from each other, this being quite in conformity with known art, and like the above-mentioned Radiometer ABL1 equipment, the blood gas measuring equipment will be adapted to automatically perform such a calibration, in this case using pre-fabricated and pre-packed reference liquids according to the invention instead of the known art reference liquids which are made ready for use in the apparatus proper.

There will now follow specific prescriptions for establishing the pH/$P_{CO_2}$ system, and then, working examples illustrating the reference liquid according to the invention will be given. It will be understood that although a very great exactitude in the parameters of the reference liquid may be obtained on the basis of the calculations stated in the following precriptions, using the empirical constants stated, the utmost exactitude of the parameters will depend on a fine adjustment performed in the particular production equipment and based partly upon empirical constants characteristic of the equipment, and partly upon corrections after control measurements against officially acknowledged standards.

Prescription 1

In a buffer system consisting of sodium bicarbonate equilibrated to a known partial pressure of $CO_2$, the pH can be calculated according to the Henderson-Hasselbalch equation:

$$pH = pK_A + \log \frac{[HCO_3^-]_a}{[CO_2]_a}$$

$pK_A$ is the thermodynamic dissociation exponent. To calculate the pH, it is necessary to correct $pK_A$ for the effect of ionic strength. This is done according to the Debye-Hückel limiting law for activity coefficients. The law is used in approximated form:

$$pK_A' = pK_A - 0.495\sqrt{\mu}$$

wherein $\mu$ is the ionic strength of the electrolytes in the solution, and 0.495 is an empirically ascertained constant. Through this, the Henderson-Hasselbalch equation becomes as follows:

$$pH = pK_A - 0.459\sqrt{\mu} + \log[HCO_3^-] - \log[CO_2]$$

wherein the quantity is in molar concentration. $[CO_2]$ is found from the equation:

$$[CO_2] = \alpha \cdot P_{CO_2} \cdot 10^{-3}$$

wherein $\beta$ is the modified Bunsen absorption coefficient.

The pH of a $24 \times 10^{-3}$ M solution of sodium bicarbonate equilibrated with a gas mixture with a partial pressure of $CO_2$ of 40 mm Hg will be 7.53. If an indifferent salt (e.g. NaCl) is added to a total ionic strength of 0.21, the pH will be 7.38.

The following constants, valid at 37° C., are used:
$pK_A = 6.33$
$\alpha = 0.032$ The prescription applies at 37° C.

The pH in a of a $12 \times 10^{-3}$ M solution of sodium bicarbonate equilibrated with a gas mixture with a partial pressure of $CO_2$ of 80 mm Hg will be 6.95.

If an indifferent salt (e.g. NaCl) is added to a total ionic strength of 0.11, the pH will be 6.84.

The same constants as above are used.

Prescription 2

When a phosphate buffer is equilibrated with $CO_2$, the pH of the buffer is changed in relation to the amount of $CO_2$. In a phosphate-bicarbonate mixture system, the following equation is established:

$$HCO_3^- + H_2PO_4^- \rightleftharpoons HPO_4^{--} + Co_2 + H_2O$$

If the initial concentrations of $HCO_3^-$, $H_2PO_4^-$ and $HPO_4^{--}$, respectively, are designated:

A, B, C the result, after mixing, is:

$$(A-a)+(B-a)\rightleftharpoons(C+a)+a$$

wherein a is the change which will bring the system into equilibrium. When carbon dioxide is added until the pressure corresponding to the concentration m, another change results:

$$(A-\alpha)+(B-\alpha)\rightleftharpoons(C+\alpha)+m$$

The mass action equation for the bicarbonate system is:

$$\frac{[H^+](A-\alpha)}{m} = K_1$$

and for the phosphate system:

$$\frac{[H^+](C + \alpha)}{(B - \alpha)} = K_2$$

Elimination of α from the equations results in:

$$\frac{([H^+] \cdot A) - (K_1 \cdot m)}{[H^+]} = \frac{(K_2 \cdot B) - ([H^+] \cdot C)}{[H^+] + K_2}$$

This results in a second degree polynomial with respect to [H+], and the pH can be calculated:

$$pH = -\log\left(\frac{K_1 \cdot m + K_2 \cdot B - K_2 \cdot A^{(\pm)}\sqrt{(K_1 \cdot m + K_2 \cdot B - K_2 \cdot A)^2 + D}}{2(C + A)}\right)$$

D=4(C+A) K₁·K₂·m
K₁ is the first acid strength constant of carbonic acid
K₂ is the second acid strength constant of phosphoric acid
A is molar concentration of bicarbonate
B is molar concentration of dihydrogen phosphate
C is molar concentration of monohydrogen phosphate.

In the calculations, the following constants are used:

$pK_1 = 6.328 - 0.495\sqrt{\mu}$ (valid at 37° C.)

$pK_2 = 7.029 - 0.594\sqrt{\mu}$ (valid at 37° C.).

In a phosphate buffer wherein C=B, μ=0.1, and the partial pressure of CO₂ is 40 mm Hg, pH will be 6.59. C=B=0.025 mol/liter.

In a phosphate buffer wherein C=4 B, and μ=0.17, and the partial pressure of CO₂ is 80 mm Hg, the pH will be 6.90. C=0.0523 and B=0.0131 mol/liter.

In both solutions, the initial concentration of bicarbonate is 0.

Prescription 3

By adding bicarbonate to the phosphate buffer solutions according to prescription 2, the pH can be varied.
A buffer consisting of C=B=0.022 M, and A=0.012 M, equilibrated with a gas mixture with a partial pressure of CO₂ of 80 mm Hg, has pH 6.84 (μ=0.1).

A buffer consisting of C=0.047 M, B=0.012 M, and A=0.022 M, equilibrated with a gas mixture having a partial pressure of CO₂ of 40 mm Hg. has pH 7.36 (μ=0.17).

Prescription 4

The sodium bicarbmate in the above prescriptions may be formed by tritration of sodium carbonate with carbon dioxide.
In this case,

|  | CO₃⁻⁻ + H⁺ ⇌ HCO₃⁻ |
|---|---|
| and | CO₂ + H₂O ⇌ H⁺HCO₃⁻ |
| the sum is: | CO₂ + H₂O + CO₃⁻⁻ ⇌ 2HCO₃⁻ |

At pH 7, the equilibrium is displaced completely to the right, as less than 0.1% of the carbonate is unconverted.

Hence, in prescription 3, the bicarbonate may by replaced with carbonate in half of the concentration to result in the same pH as calculated in prescription 3.

Prescription 5

Prescription 1 may be calculated with carbonate instead of bicarbonate. Carbonate is to be used in half of the concentration, of the reaction equilibrium in prescription 4.

Prescription 6

Bicarbmate buffer+acid, e.g. HCl [HCO₃⁻]+[CO₂]=Total concentration of "CO₂"

When the bicarbmate buffer is not prepared by equilibration with carbon dioxide, it may, for example, be prepared by addition of hydrogen ion from, e.g., hydrochloric acid, to a bicarbmate solution.

Hence, in prescription 1 80 mm Hg of $P_{CO_2}$ corresponds to 2.56×10⁻³ mol of CO₂ per liter which may be formed from bicarbmate ion by addition of acid $$HCO_3^- + H^+ = CO_2 + H_2O$$

To form 2.56×10⁻³ mol, 2.56×10⁻³ mol of H+ are required, for example in the form of HCl.
This means that (12+2.56)×10⁻³=14.56×10⁻³ mol of bicarbmate to which are added 2.56×10⁻³ mol of HCl and sodium chloride to a total ionic strength of 0.11 gives, in 1 liter of solution, a pH of 6.84.

When it is desired to prepare the liquid on the basis of carbonate, the following applies:

| CO₃⁻⁻ + H⁺ = HCO₃⁻ |
|---|
| HCO₃⁻ + H⁺ = CO₂ + H₂O |
| CO₃⁻⁻ + 2H⁺ = CO₂ + H₂O |

1 liter of solution containing (12+2.56)×10⁻³ mol of carbonate=14.56×10⁻³ mol, to which are added (14.56+2.56)×10⁻³ mol=17.12×10⁻³ mol of hydrogen ion in the form of hydrochloric acid, and sodium chloride to a total ionic strength of 0.11, also results in pH 6.84.

Prescription 7

When the buffers mentioned in prescription 3 are prepared by addition of acid in a closed container, a buffer containing C=B=0.022 and A=14.56×10⁻³ mol/liter admixed with 2.56×10⁻³ HCl per liter has pH 6.84, and the ionic strength in this solution becomes 0.1025.

When the buffer is prepared from sodium carbonate, the same amount of sodium carbonate is added, while the amount of acid is increased to (14.56+2.56)×10⁻³=17.12×10⁻³ mol of HCl per liter.

A buffer consisting of C=B=0.022 and sodium carbonate=14.56×10⁻³ mol/liter admixed with 17.12×10⁻³ mol of HCl per liter will show a pH of 6.83, as the ionic strength in this solution is increased to 0.117.

EXAMPLE 1

Bicarbonate-containing phosphate buffer with a disperse phase of fluorohydrocarbon.

The composition is:

| In the water phase: | |
|---|---|
| disodium hydrogen phosphate | 0.047 molal |
| potassium dihydrogen phosphate | 0.012 molal |
| sodium bicarbonate | 0.022 molal |
| Ponceau 4 R | 1.7 g/liter |

The water phase constitued 90% of the liquid, 10% being fluorohydrocarbon (perfluorotributyl amine) emulsified in the water phase.

This liquid is suitable for synthesizing a reference liquid having pH=7.36, $P_{CO_2}$=40 mm Hg, $P_{O_2}$=equilibrating the liquid with a gas mixture having a partial pressure of $CO_2$ of 40 mm Hg and a partial pressure of $O_2$ of 70 mm Hg at a temperature of 37° C.

EXAMPLE 2

A bicarbonate-containing phosphate buffer with a disperse phase of fluorohydrocarbon.

The composition is:

| In the water phase: | |
|---|---|
| disodium hydrogen phosphate | 0.022 molal |
| potassium dihydrogen phosphate | 0.022 molal |
| sodium bicarbonate | 0.012 molal |
| Ponceau 4 R | 1.7 g/liter |

The water phase constitutes 90% of the liquid, 10% being fluorohydrocarbon (perfluoromethyl cyclohexane) emulsified in the water phase.

This liquid is suitable for synthesizing a reference liquid having pH=6.84, $P_{CO_2}$=80 mm Hg, $P_{O_2}$=150 mm Hg, and Hb=14 g%, at 37° C., which is done by equilibrating the liquid with a gas mixture having a partial pressure of $CO_2$ of 80 mm Hg and a partial pressure of $O_2$ of 150 mm Hg at a temperature of 37° C.

EXAMPLE 3

A bicarbonate-containing aqueous phosphate buffer solution having a content of iron-phthalocyanine tetrasulfonic acid.

The composition is:

| disodium hydrogen phosphate | 0.022 molal |
|---|---|
| potassium dihydrogen phosphate | 0.022 molal |
| sodium bicarbonate | 0.012 molal |
| iron(II) phthlocynine tetra-sulfonic acid | 2% |
| iron(II) pathalocyanine tetra-sulfonic acid ($O_2$ complex) | 1% |

This solution is suitable for synthesizing a reference liquid having pH=6.84, $P_{CO_2}$=80 mm Hg, $P_{O_2}$=1 mm Hg, and Hb=0 g, at 37° C., which is done by equilibrating the solution with a gas mixture having a partial pressure of $CO_2$ of 80 mm Hg and a partial pressure of $O_2$ of 1 mm Hg at a temperature of 37° C.

EXAMPLE 4

A bicarbonate-containing phosphate buffer having a disperse phase of silicone rubber.

The composition is:

| In the water phase: | |
|---|---|
| disodium hydrogen phosphate | 0.047 molal |
| potassium dihydrogen phosphate | 0.012 molal |
| sodium bicarbonate | 0.021 molal |
| Ponceau 4 R | 1.7 g/liter |

The water phase constituted 80% of the liquid, the remaining 20% being finely dispersed silicone rubber particles (CAF4/60 "RHODORSIL").

The liquid is suitable for synthesizing a reference liquid having pH=7.36, $P_{CO_2}$=40 mm Hg $P_{O_2}$=70 mm Hg, and Hb=14 g%, t 37° C., which is done by equilibrating the liquid with a gas mixture having a $CO_2$ partial pressure of 40 mm Hg and an $O_2$ partial pressure of 70 mm Hg at 37° C.

In each of the above examples, one may, instead of the equilibration with $CO_2$, perform the addition of an acid, for example HCl, according to prescriptions 6 and 7.

We claim:

1. A stable synthetic water based reference liquid for quality control and/or calibration of blood gas measuring equipment, said liquid being enclosed in a gas-tight container and containing $HCO_3^-$ ions, $H^+$ ions, $CO_2$ gas, and $O_2$ gas plus an additional pH buffer system different from the pH buffer system constituted by the $HCO_3^-$ ions and the $CO_2$ gas, said liquid showing, at a fixed temperature, known pH, $pCO_2$ and $pO_2$ values, said liquid additionally containing oxygen reversibly contained in a dispersed non-proteinaceous organic substance which shows higher solubility for oxygen than does water, and, optionally, a coloring component showing maximum or significant absorption at about 500 nm, said organic substance being (a) a water-insoluble organic substance in which $O_2$ is soluble to an extent of at least 12% by volume at 1 atmosphere oxygen pressure and 25° C., said water-insoluble substance being a liquid of lipoid character emulsified in a liquid-in-water type emulsion, in the water base of the reference liquid, or a solid suspended in the water base of the reference liquid, or (b) an oxygen complex-forming metal organic compound of a transition group metal dissolved in the water base of the reference liquid, the stability constant of the oxygen complex of which metal organic compound is in the range of $1 \times 10^3$ to $10^{5.5}$.

2. A reference liquid as claimed in claim 1, being enclosed in the gas-tight container substantially free of gas phase.

3. A reference liquid as claimed in claim 1, wherein the organic substance is an emulsified or suspended water-insoluble substance, and is a silicone oil, a silicone rubber, a perfluorinated hydrocarbon compound or a compound containing perfluorinated hydrocarbon groups, said reference liquid being contained in a gas-tight container.

4. A reference liquid as claimed in claim 3, wherein the emulsified or suspended phase constitutes at the most 60% of the total volume.

5. A reference liquid as claimed in claim 4, wherein the emulsified or suspended phase constitutes 20–50% of the total volume.

6. A reference liquid as claimed in claim 3 wherein the compound containing perfluorinated hydrocarbon groups is perfluorotributyl amine.

7. A reference liquid as claimed in claim 6, wherein the emulsified phase constitutes 30–40% of the total volume.

8. A reference liquid as claimed in claim 1, wherein the organic substance is an oxygen complex-forming metal organic compound of a transition group metal, the stability constant of the oxygen complex of which metal organic compound is in the range of $1 \times 10^4$ to $1 \times 10^5$, said reference liquid being contained in a gas-tight container.

9. A reference liquid as claimed in claim 1, wherein the additional pH buffer system is a phosphate buffer system, said reference liquid being contained in a gas-tight container.

* * * * *

UNITED STATES PATENT AND TRADEMARK OFFICE
CERTIFICATE OF CORRECTION

PATENT NO. : 4,163,734
DATED : August 7, 1979
INVENTOR(S) : Soren Kai Sorensen et al.

It is certified that error appears in the above-identified patent and that said Letters Patent are hereby corrected as shown below:

The term of this patent subsequent to September 19, 1995 has been disclaimed.

Signed and Sealed this

Twenty-fifth Day of September 1979

[SEAL]

Attest:

Attesting Officer

LUTRELLE F. PARKER
*Acting Commissioner of Patents and Trademarks*

UNITED STATES PATENT AND TRADEMARK OFFICE
CERTIFICATE OF CORRECTION

PATENT NO. : 4,163,734

DATED : August 7, 1979

INVENTOR(S) : Soren Kai Sorensen, et al

It is certified that error appears in the above—identified patent and that said Letters Patent is hereby corrected as shown below:

The term of this patent subsequent to September 26, 1995 has been disclaimed.

THIS CERTIFICATE SUPERSEDES CERTIFICATE OF CORRECTION ISSUED September 25, 1979.

Signed and Sealed this

Twenty-second Day of July 1980

[SEAL]

Attest:

SIDNEY A. DIAMOND

Attesting Officer

Commissioner of Patents and Trademarks